(12) United States Patent
Lin et al.

(10) Patent No.: US 6,993,386 B2
(45) Date of Patent: *Jan. 31, 2006

(54) PUBLIC ACCESS DEFIBRILLATOR

(75) Inventors: Dongping Lin, Irvine, CA (US); Prabodh Mathur, Laguna Niguel, CA (US); Raul Ybarra, Newhall, CA (US)

(73) Assignee: Cardiac Science Inc., Lake Forest, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/688,362

(22) Filed: Oct. 16, 2003

(65) Prior Publication Data

US 2004/0082972 A1   Apr. 29, 2004

Related U.S. Application Data

(63) Continuation of application No. 09/591,669, filed on Jun. 12, 2000, now Pat. No. 6,658,290.

(51) Int. Cl.
*A61N 1/39*   (2006.01)

(52) U.S. Cl. ........................................................ 607/5
(58) Field of Classification Search ................. 607/4–8
See application file for complete search history.

(56) References Cited

U.S. PATENT DOCUMENTS

| 5,078,134 | A | * | 1/1992 | Heilman et al. | 607/4 |
| 6,148,233 | A | * | 11/2000 | Owen et al. | 607/5 |
| 6,289,243 | B1 | * | 9/2001 | Lin et al. | 607/5 |
| 6,405,082 | B1 | * | 6/2002 | Borgenicht | 607/5 |
| 6,597,948 | B1 | * | 7/2003 | Rockwell et al. | 607/5 |

FOREIGN PATENT DOCUMENTS

| EP | 0 671 185 A2 | * | 10/1995 |
| EP | 0 757 912 A2 | * | 12/1997 |

* cited by examiner

*Primary Examiner*—Carl Layno
(74) *Attorney, Agent, or Firm*—Gottlieb, Rackman & Reisman, P.C.

(57) ABSTRACT

A publically available external defibrillator includes a detector used to detect a life threatening condition of a patient, a controller operating the defibrillator automatically and a therapy delivery circuit that delivers appropriate therapy. The defibrillator is attached to a patient by any attendant or bystander and once it is attached, the defibrillator is adapted to monitor the patient and when a life threatening condition is detected, to apply therapy automatically, i.e., without any involvement by the patient or the attendant.

12 Claims, 4 Drawing Sheets

PUBLIC ACCESS DEFIBRILLATOR

This application is a continuation of the U.S. Ser. No. 09/591,669 filed Jun. 12, 2000, now U.S. Pat. No. 6,658,290 and incorporated herein by reference.

BACKGROUND OF THE INVENTION

A. Field of Invention

This invention pertains to an external defibrillator adapted to provide therapy selectively to patients suffering from sudden acute cardiac arrest. More particularly, the present invention pertains to an external defibrillator which is constructed and arranged to operate substantially automatically once it is positioned on the patient. The defibrillator rapidly determines the status of the patient, makes a decision on whether therapy is indicated, and, if necessary, applies such therapy until either its operation is discontinued externally or sinus rhythm has been achieved.

B. Description of the Prior Art

The term Sudden Cardiac Arrest or SCA in a patient refers to a condition characterized by a loss of effective pumping action in the heart and is generally caused by an arrhythmia. SCA results in an abrupt cessation of blood circulation to the vital organs, and once it occurs, unless the patient's heart is reverted rapidly to a sinus rhythm, death will occur. In fact SCA is considered to be the leading cause of death in the United States and throughout the world.

Arrhythmias which cause SCA include ventricular tachycardia and ventricular fibrillation. Ventricular tachycardia is characterized by electrical disturbances which cause a dangerously high cardiac rate and may lead to ventricular fibrillation. Ventricular fibrillation refers to a state where cardiac electrical activity is completely disorganized and the heart is quivering. During ventricular fibrillation, the heart does not pump blood, and no beats can be detected.

Arrhythmias may be detected from the patient's electrocardiogram (ECG), blood pressure, blood oxygenation level and other similar physiological parameters. Because the signals indicative of these parameters can be very complex, various algorithms are used to analyze these parameters to detect and classify an arrhythmia. Once detected, the arrhythmia can be eliminated by using antitachycardia therapy consisting of electrical stimulation. Two kinds of devices are presently available to provide antitachyarrhythmia therapy: internal or implanted cardioverter defibrillators (ICDs), and external defibrillators.

ICDs have been known since the early 1980s. These devices are implanted in the patient and include electrodes extending to the cardiac chambers to sense intrinsic cardiac activity and to provide stimulation signals. The intrinsic signals sensed in the cardiac chambers are used to classify the condition of the heart, and if a tachyarrhythmia is detected, then either cardioversion pacing pulses or defibrillation shocks are applied.

In order for these kinds of devices to function properly, a clinician examines the patient and, after implantation, programs a plurality of parameters into the ICD which are used by a processor to classify the condition of the patient and determine the characteristics of the stimulation signals to be applied. Frequently these parameters are selected after the patient's heart rate is increased either naturally, with exercise, or with drugs. It is advisable to re-program these parameters as the condition of the patient changes over time.

External defibrillators capable of providing defibrillation shocks or other types of therapy are also well known. Current external defibrillators must be operated manually by a trained professional such as an emergency medical technician, paramedic, firefighter, or police officer, etc. Existing external defibrillators do not monitor cardiac activity before a sudden cardiac arrest episode, and accordingly, the professional must examine the patient and determine his condition first, before any therapy is provided. Hence, inherently, the existing external defibrillators cannot be used by a layperson.

An external defibrillator described in commonly assigned U.S. Pat. No. 5,474,574 and incorporated herein by reference includes an ECG sensor and requires several parameters to be programmed by a clinician before it can be used properly. Some of the programmable parameters pertain to the sensitivity of the ECG sensor required to detect ECGs reliably. Other parameters pertain to the size, number and duration of the shocks to be applied by the device. Since these parameters must be programmed separately for each patient, by the time this defibrillator is ready to be used, it is configured to a specific patient and cannot be used for a different patient without first reprogramming its parameters.

In summary, existing external defibrillators are limited in that they must be operated by a professional, they do not have the capability to continuously monitor a patient; and they require active intervention to initiate any therapy.

There is a need for an automatic external defibrillator which can be used successfully by a layman, i.e., a person without any formal medical training.

BRIEF SUMMARY OF THE INVENTION

In view of the above, an objective of the present invention is to provide an external defibrillator which can be distributed and placed at public places which can be used effectively by a person with no special medical training.

A further objective is to provide an external defibrillator able to monitor a patient and determine automatically if a patient is in need of therapy.

A further objective is to provide an external defibrillator capable of providing cardiac therapy without requiring any information about the patient receiving it.

Yet another objective is to provide an external defibrillator which has several modes of operation so that it can be used for different purposes.

Other objectives and advantages of the invention will become apparent from the following description.

Briefly, an external defibrillator constructed in accordance with this invention includes a sensing circuit used to sense physiological signals indicative of cardiac activity, a therapy delivery circuit that generates pacing or shock pulses, and a controller that is used to operate the defibrillator automatically. Signals indicative of intrinsic cardiac activity, including R-waves and ventricular fibrillation, for example, are determined using generic criteria rather than patient-specific programming parameters. Similarly, the pulses applied to the patient to effect therapy have characteristics which are derived from general statistical data and are not patient specific. The defibrillator recognizes a life threatening cardiac condition and can apply appropriate therapy without any human input or intervention.

Optionally, the external defibrillator may include a memory for logging data for each episode during which therapy is applied. A display may also be provided to show instructions for the operation of the defibrillator and/or to selectively display the logged data. A communication module may also be provided to contact remote locations and obtain assistance for the patient.

DETAILED DESCRIPTION OF THE INVENTION

Figure 1:
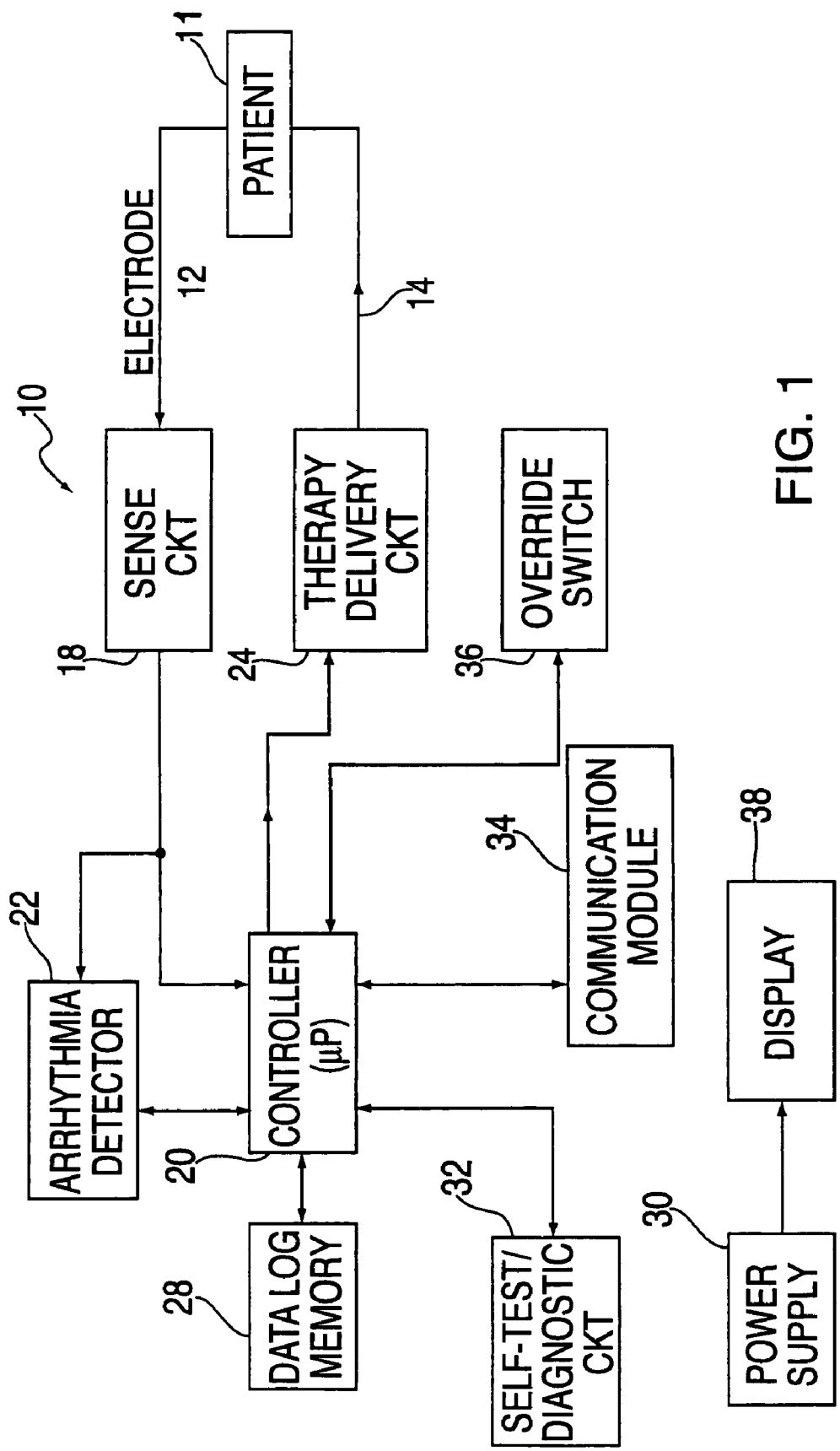
FIG. 1 shows a block diagram of an external defibrillator constructed in accordance with this invention.

Referring first to FIG. 1, an external defibrillator 10 constructed in accordance with this invention may include several subsystems as described below, it being understood that not all the subsystems are necessary for the system to operate. Generally speaking, the defibrillator 10 is coupled to patient 11 by electrodes strategically placed on the patient's body to permit the defibrillator 10 to collect information from the patient regarding his current status and to deliver therapy. For the sake of simplicity, FIG. 1 shows symbolically two electrodes 12 and 14 being used to detect signals indicative of the cardiac condition of the patient and to deliver therapy, respectively, it being understood that more electrodes may be required to perform these functions, and that some electrodes may be used for both these functions.

The signals acquired by electrode 12 are received by a sense circuit 18 which analyzes these signals and determines various cardiac parameters, such as the current cardiac rhythm. This information is fed to the controller 20. The controller, a microprocessor, uses the parameters received from the sense circuit 18 together with other information to determine the current condition of the patient. For this purpose the controller 20 provides the parameters to an arrhythmia detector 22. For the sake of clarity, this detector is shown in FIG. 1 as a separate subsystem, but preferably it is implemented as software within the controller 20. Once the controller determines that therapy is required, it activates a therapy delivery circuit 24 which then delivers suitable shocks or other electrical signals through electrode 14.

Information obtained from or about the patient, as well as data regarding therapy applied to the patient, is logged by a data logging circuit 28. Some of this information may be downloaded to a printer or shown on a display if so desired.

Power to the defibrillator is provided by a power supply 30 which may include rechargeable or replaceable batteries.

A self-test and diagnostic circuit 32 is used to monitor the other subsystems of the defibrillator as described below. For example, the circuit 32 may monitor the power supply 30. If it determines that the power supply has a low energy backup capability, it may disable the therapy delivery circuit but allow continued monitoring of the patient. If the power supply level is very low, the circuit 32 may shut down the whole defibrillator.

Circuit 32 may also monitor the coupling between the electrodes and the corresponding organ tissues. For example, circuit 32 may determine the impedance between the two electrodes. If this impedance is too high, the defibrillator may be inhibited from operating.

Circuit 32 may also include a watchdog circuit (not shown) which is adapted to receive a signal from the controller 20 at predetermined intervals. In the absence of these signals, the watchdog circuit 32 determines that the controller 20 is inoperative and may shut down the defibrillator. The other elements and subsystems of the defibrillator 10 may be monitored by the circuit 32 in the same manner.

A communication module 34 is used to establish communication with the outside world and to provide information to a remote device about the current operation and status of the defibrillator 10. For example, the communication module 34 may include a cellular telephone capable of accessing an emergency number associated with a police station or an emergency room. Preferably, the communication module 34 also includes a means of identifying the location of the defibrillator 10 to the remote device. This means may include a Global Positioning System (GPS) or other geographic locating systems.

Figure 2:
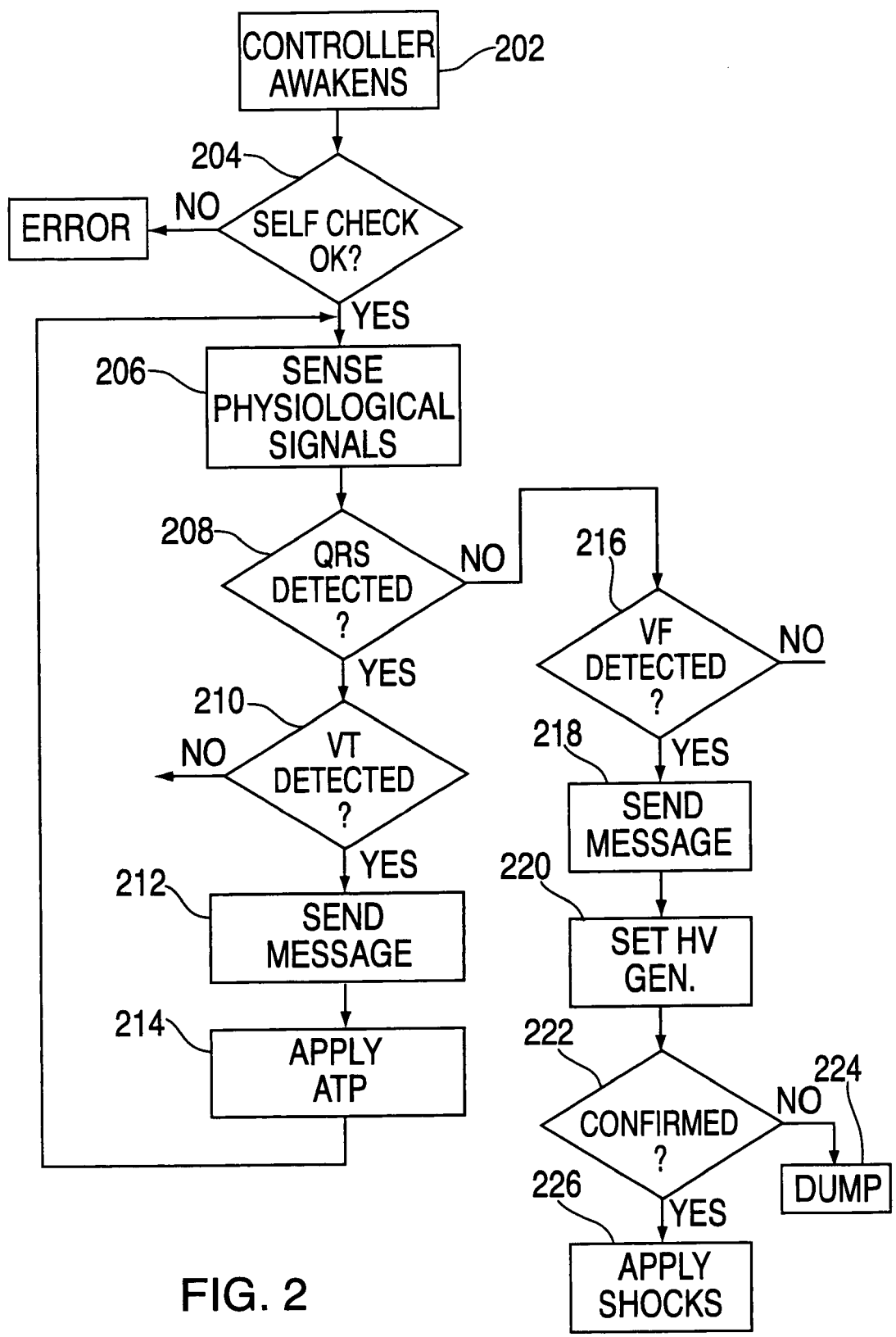
FIG. 2 shows a flow chart for the operation of the defibrillator of FIG. 1.

The operation of the defibrillator is now discussed in conjunction with the flow chart of FIG. 2. While other modes of operation are also possible, preferably the defibrillator 10 operates in a completely automatic mode in which, once it is attached to the patient, does not require any intervention from the patient or an attendant. Therefore, the defibrillator can be used by virtually anyone, with no training required. For the purposes of this flow chart in the following scenario it is assumed that a patient has suffered a sudden cardiac arrest. A passerby notices that the patient is in distress and that an automatic defibrillator is nearby. The passerby attaches the electrodes of the defibrillator to the chest of the patient in accordance with instructions on the defibrillator, and he then activates a switch 36 indicating that the defibrillator 10 is properly in place. The activation of switch 36 awakens the controller 20 (step 202).

In step 204 the self-test/diagnostic circuit 32 (FIG. 1) is activated. The circuit 32 checks the power reserves of power supply 30, the impedance between the electrodes 12 and 14, and any other critical portions of the system that may require attention. If during this self-check an abnormal condition is detected, an error indication is generated and the operation of the defibrillator 10 is halted. For example, if the impedance between the electrodes is too high, a message may be generated requesting that the electrodes be repositioned. Similarly, if the power supply voltage is determined to be too low, then a message may be generated indicating that new batteries are required. These messages may be shown in the display 38 (FIG. 1). Additionally, or alternatively, an audio signal may be activated whenever the self-test indicates a problem with the system. The self test and diagnostic circuit 32 (FIG. 1) may operate at regular intervals once the defibrillator is activated.

Figure 3:
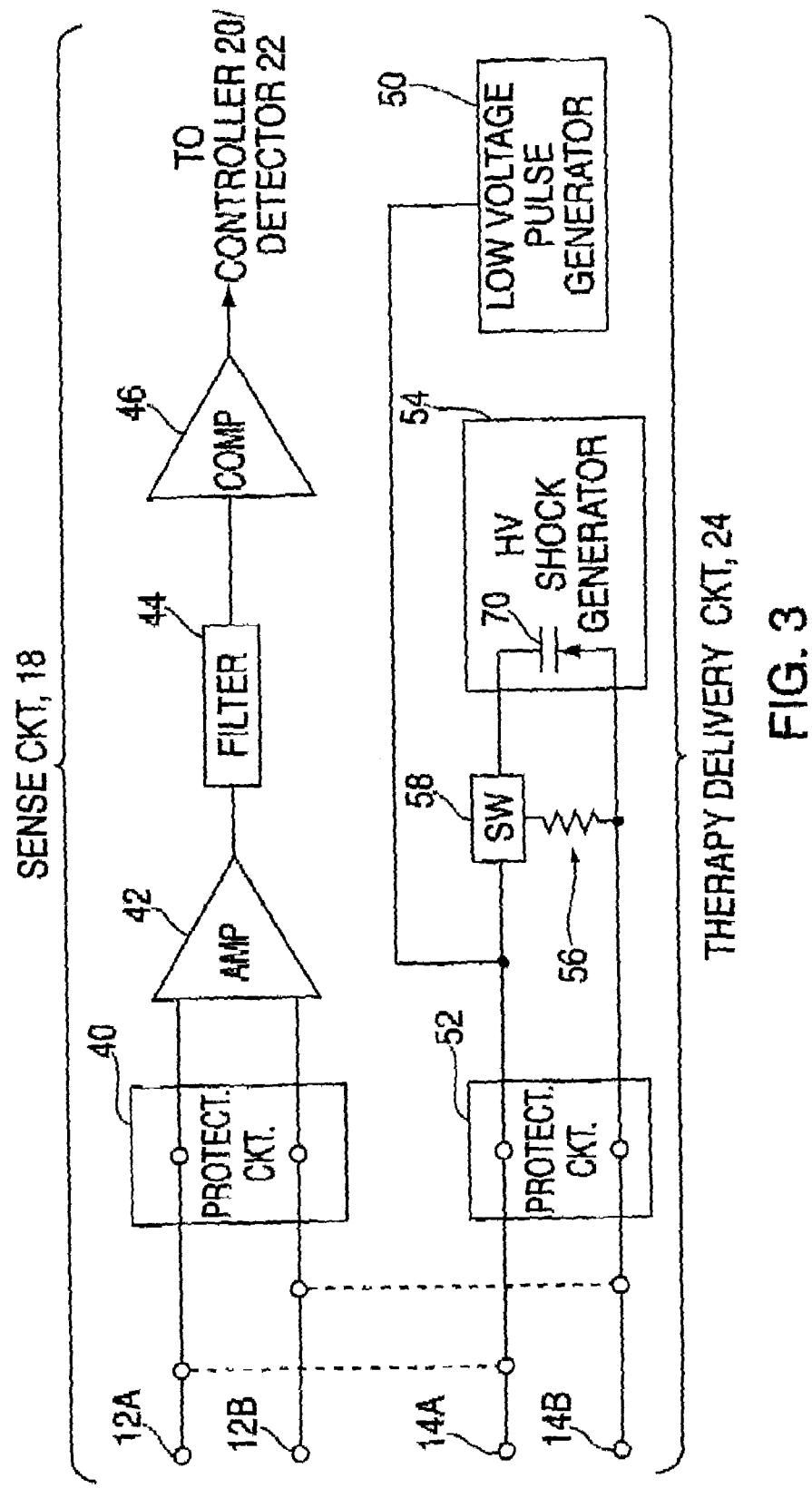
FIG. 3 shows a block diagram of the sense and the therapy delivery circuits of FIG. 1.

If the self-test step 204 indicates that the defibrillator is operational, then in step 206 the sense circuit 18 is activated to determine the current cardiac activity. As mentioned above, there are many physiological signals that can be used to perform this function, such as the ECG, blood pressure, pulse oximetry, and so on. In the present description, it is assumed that the ECG is analyzed. As shown in FIG. 3, two electrodes 12A and 12B are used to measure the ECG. These electrodes are attached across the chest of the patient in a well-known manner. The two electrodes 12A, 12B are connected to a protection circuit 40. The purpose of the protection circuit 40 is to isolate the defibrillator 10 electrically from the patient and other sources of electrical signals. The signals from the electrodes 12A, 12B pass through the protection circuit 40 and then are amplified by an amplifier stage 42. After amplification, the signals pass through a filter stage 44 which eliminates noise from the signals. The filtered signals are next fed to a comparator stage 46 which insures that the signals fall within a predetermined range. The resulting signals are then sent to the controller 20 and arrhythmia detector 22.

Figure 4:
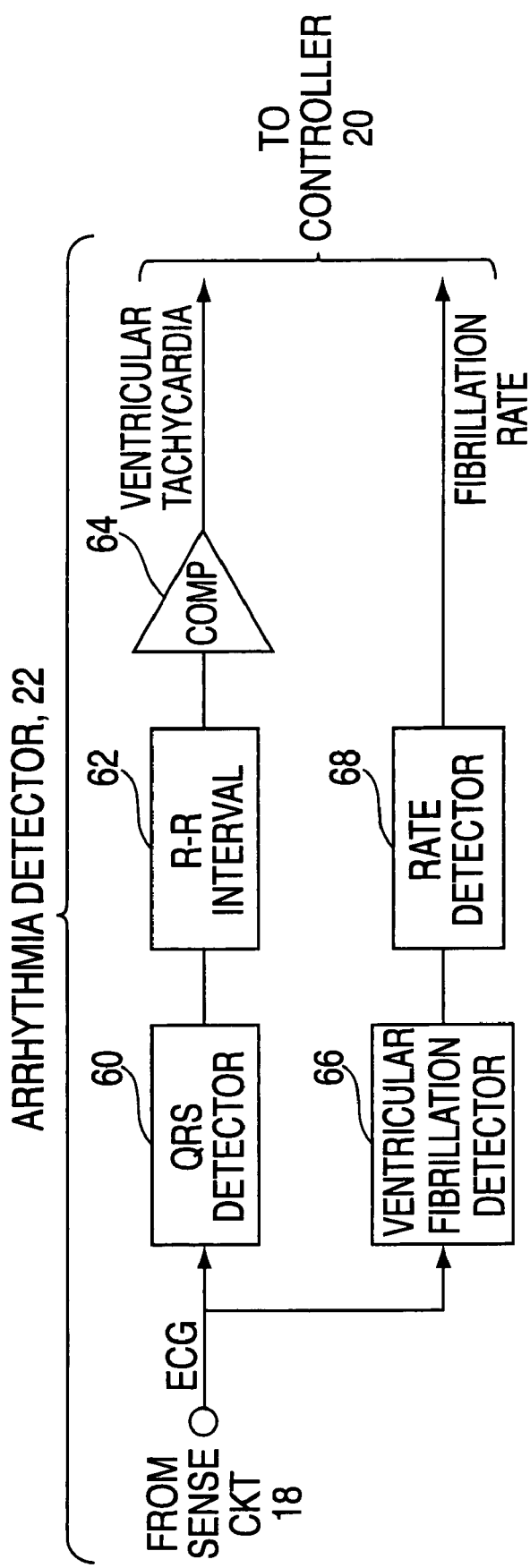
FIG. 4 shows a block diagram of the arrhythmia detector of FIG. 1.

Referring now to FIG. 4, the arrhythmia detector 22 includes a QRS detector 60 adapted to detect a QRS complex. Since the defibrillator 10 has no information specific to the patient, the QRS detector must use generic criteria for detecting the QRS complexes, based, for example, on statistical information collected from other patients. Once a QRS complex is detected, a signal is sent to an R-R interval calculator 62 which uses the QRS complexes to calculate successive R-R intervals. The current R-R interval is provided to a comparator 64 which uses certain generic criteria to determine if the patient is suffering from ventricular tachycardia.

A combination of heart rate and morphology analysis is used to detect ventricular tachycardia. A rhythm is classified as ventricular tachycardia when the heart rate is higher than ventricular tachycardia detection rate but lower than ventricular fibrillation detection rate and the morphological analysis indicate wide QRS complex.

Once ventricular tachycardia is detected, its rate is determined by rate detector 68 and this rate is provided to the controller 20.

In addition, the detector 22 may also include a ventricular fibrillation detector 66 which analyzes the ECG signals from sense circuit 18 to detect ventricular fibrillation.

Ventricular fibrillation is detected when the heart rate excesses the ventricular fibrillation rate or when the heart rate is irregular and the rhythm is proceeded by a shockable rhythm, which can be either ventricular tachycardia or ventricular fibrillation.

Other analysis methods for signal processing can be used for detecting life threatening arrhythmias, for examples, R-R interval variability, amplitude variability, amplitude distribution analysis, probability density function, template matching, on-set analysis, signed or unsigned area under the curve, waveform factor, complexity analysis, modular domain function, frequency domain analysis, Q-T interval analysis, and S-T analysis.

Returning to FIG. 2, in step 206 the sense circuit 18 detects intrinsic cardiac signals, as discussed above. In step 208 these signals are analyzed by the QRS detector. If a QRS complex is detected, in step 210 the R-R interval calculator and comparator 64 (FIG. 4) determines whether life-threatening ventricular tachycardia (VT) is present. If in step 210 VT is not detected then it tests to see if the amplitude is less than a threshold, e.g. 0.2 millivolts. If the amplitude is less than the threshold, the rhythm is classified as fine ventricular fibrillation if it is proceeded by a shockable rhythm and the rhythm is classified as asystole if it is proceeded by a nonshockable rhythm.

If in step 210 VT is detected, and if controller 20 is equipped with a communication module 34, then in step 212 the controller 20 activates the communication module 30 to send a message to a service center, e.g. a police station and/or an emergency room that an emergency condition exists and that the defibrillator 10 is preparing to apply anti-tachycardia therapy.

FIG. 3 also shows details of the therapy delivery circuit 24. The circuit 24 includes a low-voltage pulse generator 50 receiving commands from controller 20 and generating antitachycardia pacing pulses. These pulses are fed through a protection circuit 52 to a pair of output electrodes 14A, 14B. The protection circuit 52 is used to isolate the circuit 24 from the patient.

Therapy circuit 24 further includes a high voltage shock generator 54, with or without a charge dump resistor 56 and an electronic switch 58. The generator 54 and switch 58 are responsive to commands from controller 20. When the high voltage shock generator 54 receives a command from the controller 20 indicating that a shock may be required, the generator charges an internal capacitor (70) to a predetermined voltage. This capacitor 70 can be selectively discharged either to electrodes 14A, 14B or to a charge dissipating resistor 56 by switch 58 depending on the commands issued by controller 20.

Referring back to FIG. 2, in step 214, the controller 20 generates a command to apply antitachycardia therapies, e.g. pacing pulses or cardioversion shocks. In response, the generator 50 generates antitachycardia therapies to the electrodes 14A, 14B. Preferably these antitachycardia therapies are generated and applied synchronously with the detected QRS complexes. More particularly, each pacing pulse or cardioversion shock may be applied within a specified time, e.g. 60 milliseconds after a QRS complex (or R-wave) to insure that the therapy is not applied during a T-wave. This type of synchronized ventricular tachycardia therapy is important because it has been found that a therapy delivered on a T-wave can induce ventricular fibrillation, a condition worse than ventricular tachycardia. In some prior-art external defibrillators, a manual synchronizing button was provided. The present defibrillator is superior to these prior art defibrillators because it synchronizes automatically anti-tachycardia therapy, either pacing or cardioversion, to the R-waves, thereby advantageously reducing the chances of inducing ventricular fibrillation. This mode is further advantageous because it reduces the delay in applying therapy to the patient and it eliminates possible operator error.

If in step 208 a QRS complex is not detected, then in step 214 the ventricular fibrillation detector 66 (FIG. 4) and rate detector 68 are used to detect a life threatening ventricular fibrillation. In the presence of this condition, in step 218 a message is sent indicating that defibrillation shock therapy is required.

In step 220, the controller 20 (FIG. 1) sends a command to the high voltage shock generator 54 (FIG. 3) to set the HV generator and to cause it to charge its capacitor 70. In step 222 a reconfirmation step is provided. In this step a final decision is made as to whether a high-level defibrillation shock is required. One criteria for this determination may be to check the output of rate detector 68 (FIG. 4) to determine if a life threatening ventricular fibrillation is still present. Another criterion could be to check whether switch 36 (FIG. 1) has been activated. This switch 36 now may be activated, for example, by the patient, if conscious, or by the attendant in the case that the defibrillation shock is not required. If in step 222 it is determined that a fibrillation shock is not necessary, then in step 224 the energy of internal capacitor 70 is dumped by switch 58 through resistor 56 (FIG. 3). Otherwise, in step 226 a shock is applied through the protective network 52 (FIG. 3) and electrodes 14A, 14B, to the patient. A cardioversion or defibrillation shock can be either mono-phasic or multi-phasic. Again, the parameters for the cardioversion and defibrillation shocks can be generic or can be patient specific. Preferably each therapy is delivered synchronously with the cardiac fibrillations if possible.

In another embodiment, the detection circuit can have only one indicative signal for all life threatening arrhythmias, which include ventricular tachycardia and ventricular fibrillation. A therapy is delivered to the patient as either synchronized cardioversion to an R wave or asynchronized defibrillation if no R waves are found.

In FIGS. 1, 3 and 4, separate electrodes 12, 14 or corresponding electrode pairs 12A, 12B and 14A, 14B of the sensing circuit 18 or therapy delivery circuit 24 are shown as being used to acquire signals from the heart and to deliver therapy. However, a single pair or set of electrodes may be used to perform both functions.

Once the controller 20 becomes active and the defibrillator 10 has passed the self-test step 204, its operation is automatically logged in the data log memory 28. The logging includes details of the QRS complexes sensed, the ventricular tachycardia or fibrillation rates, and a history of the therapy applied to a patient. This information may be selectively uploaded from data log memory 28 to a separate location. In addition, the defibrillator 10 may be provided with the display 38 which may be used to provide instructions for the operation of the defibrillator 10 or to display the data logged in memory 28. The memory 28 may include a hard disk, an optical disk, a solid state memory, a flash card, a CD recorder or a combination of any of these devices.

In summary, an external defibrillator is described herein which can provide automatic therapy to patients with life threatening arrhythmias or sudden cardiac arrest. Any person can attach the device to the patient since no special training is required. Once the defibrillator is properly attached to the patient, the condition of the patient is continuously and automatically monitored. The defibrillator analyzes physiological signals of the patient to automatically detect an arrhythmia and deliver therapy to the patient if necessary, using generic criteria. An important feature of the invention is that it is based on a programmable controller whose programming parameters are not customized for each patient, but instead contain generic parameters which allow the defibrillator to operate effectively for any patient. Consequently, the defibrillator can be effective without reprogramming between patients.

Although the main operation mode is fully automatic, different operation modes, such as advisory or manual, can be included to provide a trained operator the control to the device.

The defibrillator performs a self-test to insure that all its components/subassemblies and the connections to the patient are operational. When the self-test and diagnostic circuit detects a malfunction, a visual indication and/or an audio signal can indicate that the defibrillator is not operational.

The defibrillator may be provided with a display for showing instructions, error messages, data descriptive of the patient's current/past condition, and the therapy applied by the defibrillator.

A communication module may be also be provided within the defibrillator to alert personnel at a remote location that the patient has experienced a life threatening episode and that therapy is being delivered by the automatic defibrillator. Emergency personnel (such as an ambulance) may be dispatched to provide assistance. Data from the data logging memory may also be transmitted at the same time. The communication module may include a locator unit such as a GPS (Global Positioning System) which can provide the physical location of the patient. The communication module may make use of a cellular telephone system, wireless radio or telephone system, a controller network, the Internet, and so on. The communication module may also be activated by the self-test and diagnostic circuit if tests show that the defibrillator needs servicing or repair.

The sensing of physiological signals and therapy can be affected on different electrodes dedicated for each of these functions, or can be aeffected on a single set of electrodes.

Obviously, numerous modifications may be made to this invention without departing from its scope as defined in the appended claims.

We claim:

1. A publicly accessible external defibrillator for automatically generating a generic cardiac therapy for a person suffering from a life threatening cardiac condition, said external defibrillator comprising;
    a first electrode adapted to be attached to said patient;
    a detector circuit coupled to said first electrode and adapted to detect a life threatening cardiac condition based on a physiological signal sensed through said electrode, said detector circuit detecting said cardiac condition using non-patient specific criteria;
    a microprocessor-based controller coupled to said detector circuit and adapted to generate a command in the presence of said life threatening condition;
    a pulse generator adapted to generate therapeutic pulses selected to a pulse generator adapted to generate therapeutic pulses selected to terminate said life threatening cardiac condition in response to said command, said pulse generator operating in at least one of an automated mode in which therapy is applied automatically to the patient and an advisory mode in which an indication is generated to indicate that therapy is available and can be applied;
    a self-test and diagnostic circuit adapted to run tests on said external defibrillator to determine if said external defibrillator is operational; and
    a communications module, said controller being adapted to send a message automatically to a remote location through said communication module when said life threatening condition is detected, said message indicating one of the occurrence and detection of said condition and the patient's location;
    wherein said detector circuit is adapted to detect intrinsic cardiac signals and said controller is adapted to automatically generate said command in synchronism with said intrinsic cardiac signals.

2. The external defibrillator of claim 1 further comprising a second electrode attached to said patient and being coupled to said pulse generator to deliver said therapeutic pulses to the patient's heart.

3. The external defibrillator of claim 1 wherein said first electrode is coupled to said pulse generator to deliver said therapeutic pulses to the patient's heart.

4. The external defibrillator of claim 1 further comprising a sensor circuit coupled to said first electrode to sense intrinsic cardiac signals, said sensor circuit being adapted to transmit said intrinsic cardiac signals to said detector circuit.

5. The external defibrillator of claim 1 wherein said detector circuit is adapted to monitor the heart automatically and continuously after said electrode is attached to said patient.

6. The external defibrillator of claim 1 further comprising a data logging memory for logging information descriptive of said life threatening condition and the therapy delivered to revert said life threatening condition.

7. The external defibrillator of claim 1 further comprising a display, wherein said controller is adapted to provide on said display at least one of an instruction for the operation of the defibrillator and information indicative of a condition of the patient.

8. The external defibrillator of claim 1 wherein said controller defines a manual mode of operation, where the operator has the full control in delivering therapy.

9. A publicly accessible external defibrillator for automatically generating a generic cardiac therapy for a person suffering from a life threatening cardiac condition, said external defibrillator comprising;
- a first electrode adapted to be attached to said patient;
- a detector circuit coupled to said first electrode and adapted to detect a life threatening cardiac condition based on a physiological signal sensed through said electrode, said detector circuit detecting said cardiac condition using non-patient specific criteria;
- a microprocessor-based controller coupled to said detector circuit and adapted to generate a command in the presence of said life threatening condition;
- a pulse generator adapted to generate therapeutic pulses selected to a pulse generator adapted to generate therapeutic pulses selected to terminate said life threatening cardiac condition in response to said command, said pulse generator operating in at least one of an automated mode in which therapy is applied automatically to the patient and an advisory mode in which an indication is generated to indicate that therapy is available and can be applied;
- a self-test and diagnostic circuit adapted to run tests on said external defibrillator to determine if said external defibrillator is operational; and
- an inhibit switch which may be operated by the patient or an attendant, and wherein said controller is adapted to delay said command if said inhibit switch has been activated to protect said patient from undesirable therapeutic pulses;
- wherein said detector circuit is adapted to detect intrinsic cardiac signals and said controller is adapted to automatically generate said command in synchronism with said intrinsic cardiac signals.

10. A publicly accessible external defibrillator for automatically generating a generic cardiac therapy for a person suffering from a life threatening cardiac condition, said external defibrillator comprising:
- a first electrode adapted to be attached to said patient;
- a detector circuit coupled to said first electrode and adapted to detect a life threatening cardiac condition based on a physiological signal sensed through said electrode, said detector circuit detecting said cardiac condition using non-patient specific criteria;
- a microprocessor-based controller coupled to said detector circuit and adapted to generate a command in the presence of said life threatening condition;
- a pulse generator adapted to generate therapeutic pulses selected to a pulse generator adapted to generate therapeutic pulses selected to terminate said life threatening cardiac condition in response to said command, said pulse generator operating in at least one of an automated mode in which therapy is applied automatically to the patient and an advisory mode in which an indication is generated to indicate that therapy is available and can be applied; and
- an inhibit switch which may be operated by the patient or an attendant, and wherein said controller is adapted to delay said command if said inhibit switch has been activated to protect said patient from undesirable therapeutic pulses.

11. A publicly accessible external defibrillator for automatically generating a generic cardiac therapy for a person suffering from a life threatening cardiac condition, said external defibrillator comprising:
- a first electrode adapted to be attached to said patient;
- a detector circuit coupled to said first electrode and adapted to detect a life threatening cardiac condition based on a physiological signal sensed through said electrode, said detector circuit detecting said cardiac condition using non-patient specific criteria;
- a microprocessor-based controller coupled to said detector circuit and adapted to generate a command in the presence of said life threatening condition; and
- a pulse generator adapted to generate therapeutic pulses selected to a pulse generator adapted to generate therapeutic pulses selected to terminate said life threatening cardiac condition in response to said command, said pulse generator operating in at least one of an automated mode in which therapy is applied automatically to the patient and an advisory mode in which an indication is generated to indicate that therapy is available and can be applied; and
- a communication module, said controller being adapted to send a message automatically to a remote location through said communication module when said life threatening condition is detected, said message indicating one of the occurrence and detection of said condition and the patient's location.

12. A publicly accessible external defibrillator for automatically generating a generic cardiac therapy for a person suffering from a life threatening cardiac condition, said external defibrillator comprising:
- a first electrode adapted to be attached to said patient;
- a detector circuit coupled to said first electrode and adapted to detect a life threatening cardiac condition based on a physiological signal sensed through said electrode, said detector circuit detecting said cardiac condition using non-patient specific criteria;
- a microprocessor-based controller coupled to said detector circuit and adapted to generate a command in the presence of said life threatening condition; and
- a pulse generator adapted to generate therapeutic pulses selected to a pulse generator adapted to generate therapeutic pulses selected to terminate said life threatening cardiac condition in response to said command, said pulse generator operating in at least one of an automated mode in which therapy is applied automatically to the patient and an advisory mode in which an indication is generated to indicate that therapy is available and can be applied; and
- a data logging memory for logging information descriptive of said life threatening condition and the therapy delivered to revert said life threatening condition.

* * * * *